United States Patent [19]

Sato et al.

[11] Patent Number: 4,646,724
[45] Date of Patent: Mar. 3, 1987

[54] ENDOSCOPIC PHOTOGRAPHING APPARATUS

[75] Inventors: Ken Sato; Yutaka Takahashi; Takashi Tsukaya; Shinichi Kato; Shinichiro Hattori, all of Tokyo, Japan

[73] Assignee: Olympus Optical Co., Ltd., Tokyo, Japan

[21] Appl. No.: 817,168

[22] Filed: Jan. 9, 1986

Related U.S. Application Data

[63] Continuation of Ser. No. 540,830, Oct. 11, 1983, abandoned.

[30] Foreign Application Priority Data

Oct. 15, 1982 [JP] Japan ................................ 57-180820
Oct. 15, 1982 [JP] Japan ................................ 57-180849
Oct. 15, 1982 [JP] Japan ................................ 57-180851
Oct. 15, 1982 [JP] Japan ................................ 57-180852

[51] Int. Cl.⁴ .............................................. A61B 1/06
[52] U.S. Cl. ......................................... 128/6; 354/62
[58] Field of Search ........................................ 128/4–8; 354/62; 358/98, 901

[56] References Cited

U.S. PATENT DOCUMENTS

| 4,074,306 | 2/1978 | Kakinuma et al. | |
| 4,248,213 | 2/1981 | Landre | 358/98 |
| 4,253,447 | 3/1981 | Moore et al. | |
| 4,261,344 | 4/1981 | Moore et al. | |
| 4,325,618 | 4/1982 | Hosoda | 128/6 |
| 4,349,014 | 9/1982 | Takamatsu | 128/6 |
| 4,423,436 | 12/1983 | Kimura | 358/98 |
| 4,429,686 | 2/1984 | Hosoda | 128/6 |
| 4,475,539 | 10/1984 | Konomura | 128/6 |
| 4,487,489 | 12/1984 | Takamatsu | 128/6 |

FOREIGN PATENT DOCUMENTS 0018126 10/1980 European Pat. Off. ................ 128/6

Primary Examiner—Edward M. Coven
Assistant Examiner—Max F. Hindenburg
Attorney, Agent, or Firm—Frishauf, Holtz, Goodman & Woodward

[57] ABSTRACT

An endoscopic photographing apparatus has a TV camera with a CCD image sensor which is mounted on an eyepiece section of an endoscope, a light flash source for supplying a light flash as photographing light to the endoscope, and an observation light source for supplying observation light. The light flash source is turned on in synchronism with a release signal and a transfer gate pulse for the video signal, at the time of still image photographing. The photographic field of view of the TV camera is darkened for at least one-field scanning period, before the light flash source is turned on.

19 Claims, 8 Drawing Figures

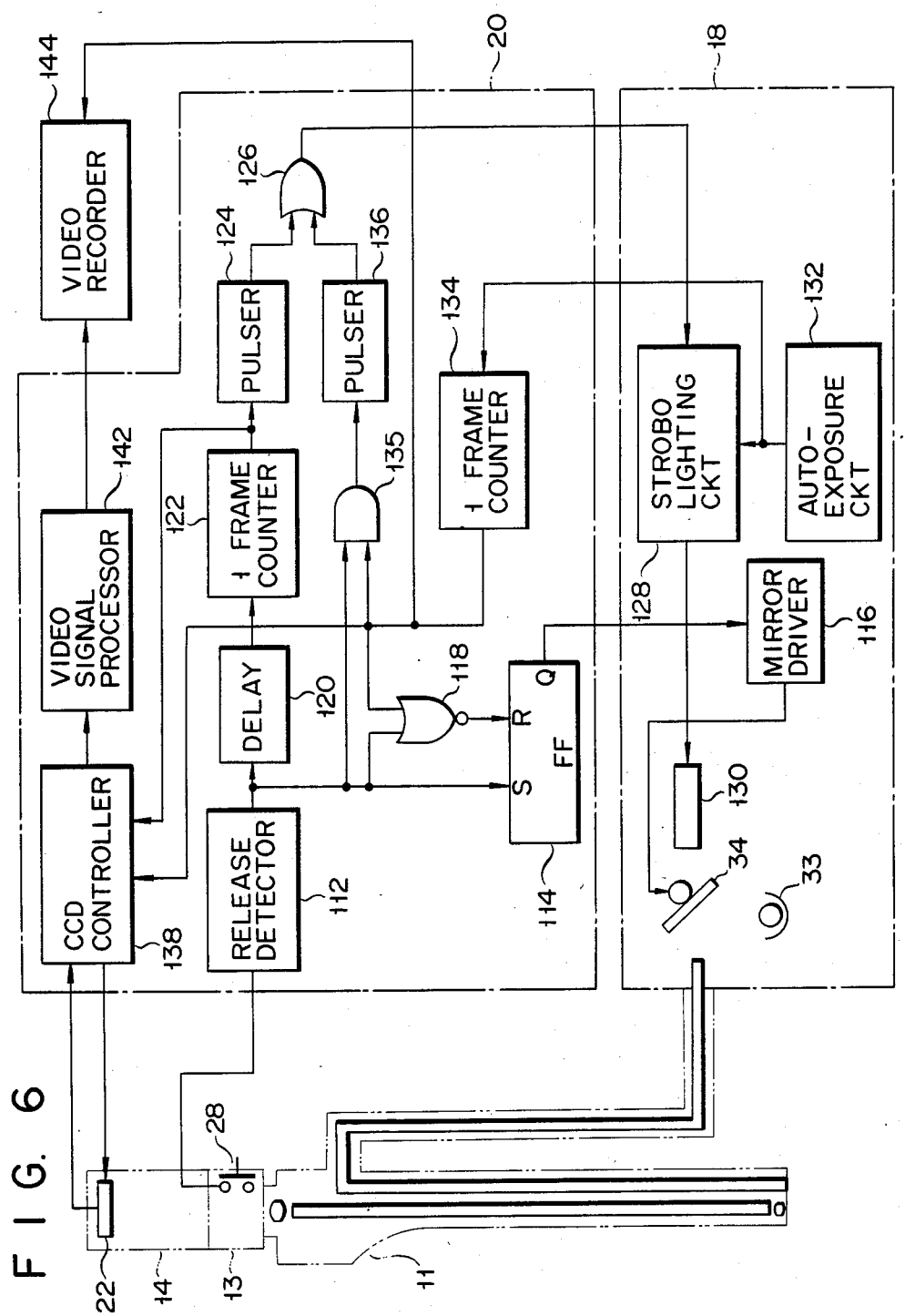
F I G. 6

ENDOSCOPIC PHOTOGRAPHING APPARATUS

This application is a continuation of application Ser. No. 540,830, filed Oct. 11, 1983, now abandoned.

BACKGROUND OF THE INVENTION

The present invention relates to an endoscopic photographing apparatus using a solid state image sensor.

A TV camera having a solid state image sensor has been used to observe or photograph an endoscopic body cavity image. An object to be examined is illuminated by an observation lamp such as a halogen lamp in order to observe it for immediate diagnosis. However, the object must be illuminated by a strobe light source such as a xenon lamp in order to photograph it to obtain a still image for record or later diagnosis. In this manner, the light sources are switched in accordance with the observation mode and the still image photographing mode.

In the endoscopic photographing apparatus, the TV camera performs interlaced scanning at a speed of 1/60 sec (about 16.7 msec (millisecond)). The strobe light source flashes within a range between several hundred microseconds and 10 msec in the automatic flash mode. When the strobe light source flashes for a maximum period of 10 msec, this period comes close to the scanning time (16.7 msec). When the flashing start moment of the strobe light source considerably deviates from the scanning start moment of one field, the light rays from the strobe light source cannot be effectively utilized. Furthermore, when the diagnostic light source (observation mode) is switched to the strobe light source (still image photographing mode), light rays from these two light sources are mixed, resulting in a foggy image. As a result, a clear image cannot be obtained. In addition to this disadvantage, when the strobe flashing period is set to be shortest (e.g., when the strobe light source flashes for 1/1000 sec or less), 90% or more of the exposure time (1/60 sec) becomes an idle time which cannot be used for charge storage. During this nonstorage time, the stored charge distribution changes due to a dark current. As a result, a good video image cannot be obtained.

SUMMARY OF THE INVENTION

It is an object of the present invention to provide an endoscopic photographing apparatus for controlling light emission of a light source so as to improve the quality of a resultant image.

According to an aspect of the present invention, there is provided an endoscopic photographing apparatus having a circuit for causing a photographing light source, i.e., an electronic flash tube, to emit light in synchronism with a transfer gate signal supplied after a release signal is generated.

According to another aspect of the present invention, there is also provided an endoscopic photographing apparatus having a circuit for stopping light emission of the light source to darken a photographic field of view for at least one-field scanning time or over one-frame scanning time before a still image is photographed.

According to still another aspect of the present invention, there is also provided an endoscopic photographing apparatus having a circuit for displaying an image for a period in which the photographic field of view is darkened, the image being obtained before the photographic field of view is darkened.

According to still another aspect of the present invention, there is also provided an endoscopic photographing apparatus having a circuit for transferring charge stored on the solid state image sensor immediately after the electronic flash tube flashes.

BRIEF EXPLANATION OF THE DRAWINGS

FIG. 6 is a block diagram of an endoscopic photographing apparatus according to still another embodiment of the present invention;

DETAILED DESCRIPTION OF THE PREFERRED EMBODIMENTS

Figure 1:
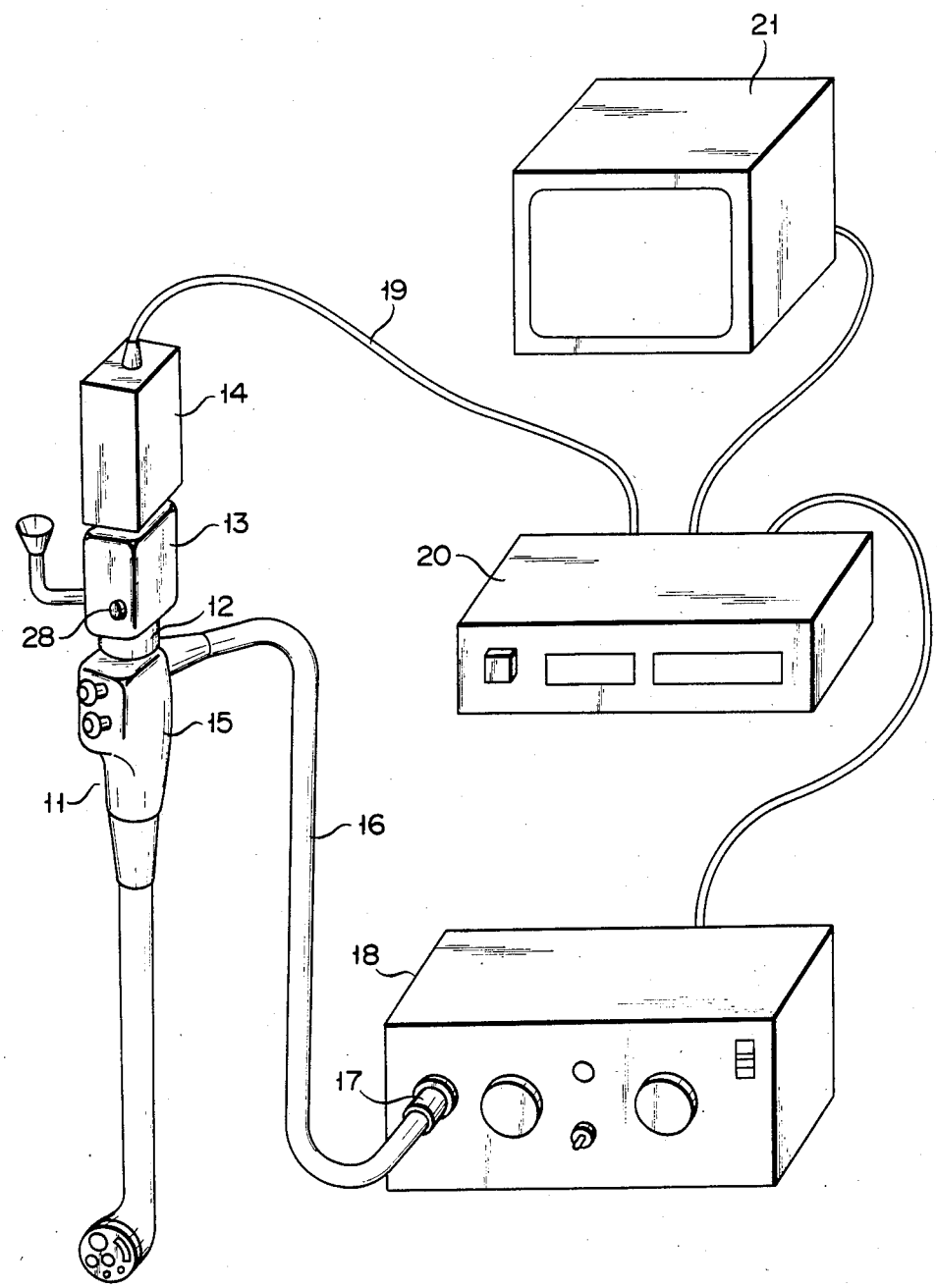
FIG. 1 is a perspective view of an endoscopic photographing apparatus according to an embodiment of the present invention.

Referring to FIG. 1, a solid state TV camera 14 is mounted on an eyepiece section 12 of an endoscope 11 through a TV adapter 13. A connector 17 at the distal end of a universal cord 16 extending from an operation section 15 of the endoscope 11 is connected to the socket of a light supply unit 18. A cord 19 extending from the TV camera 14 is connected to a camera control unit (CCU) 20. The CCU 20 is connected to a CRT display 21 and the light supply unit 18.

Figure 2:
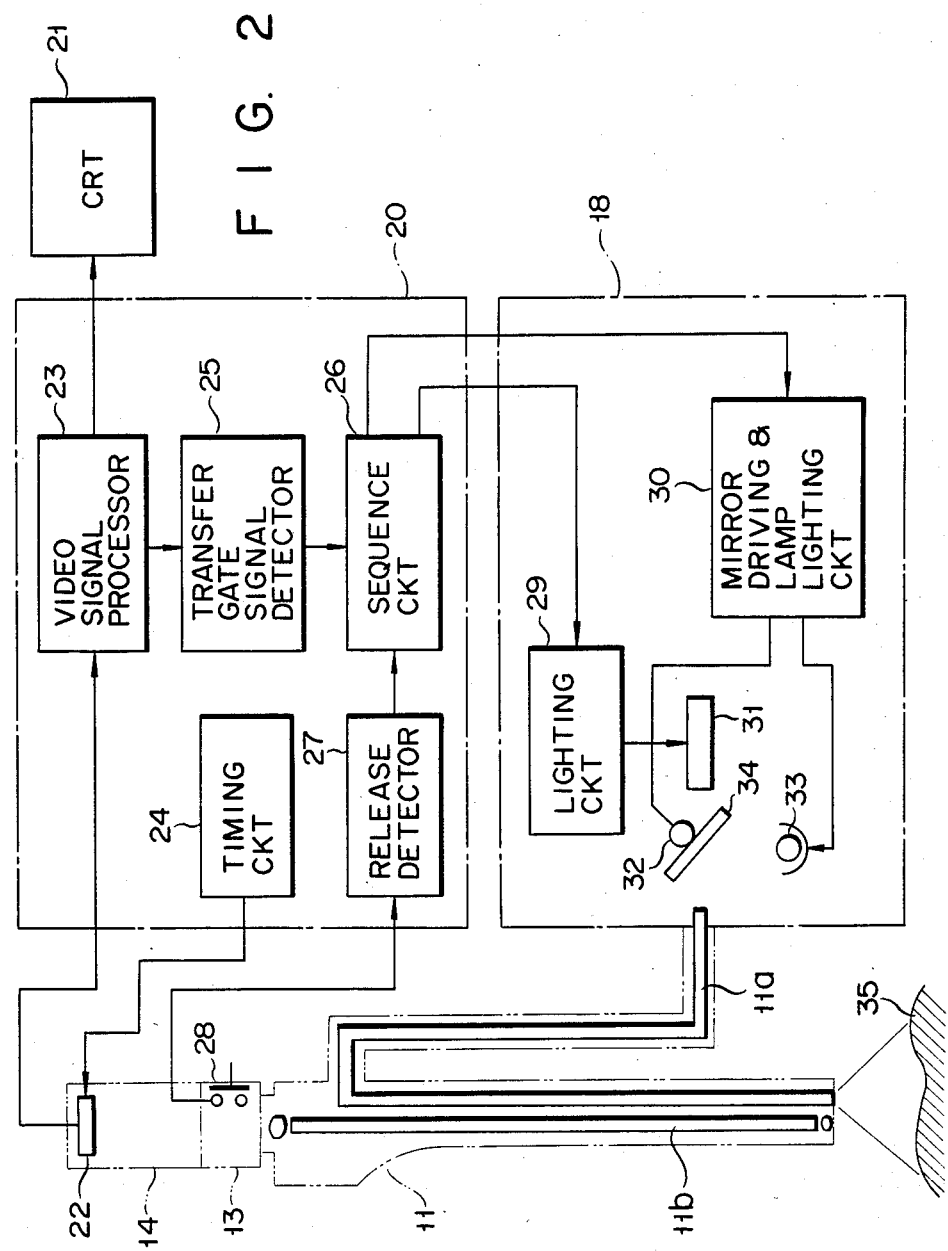
FIG. 2 is a block diagram of the endoscopic photographing apparatus shown in FIG. 1.

Referring to FIG. 2, the solid state image sensor, e.g., a charge coupled device (CCD) 22, of the TV camera 14 is connected to the input terminal of a video signal processor 23 of the CCU 20. The CCD 22 is also connected to the output terminal of a timing circuit 24. The output terminals of the video signal processor 23 are connected to the CRT display 21 and to the input terminal of a transfer gate signal detector 25. The output terminal of the gate signal detector 25 is connected to an input terminal of a sequence circuit 26. The output terminal of a release detector 27 is connected to another input terminal of the sequence circuit 26. The release detector 27 serves to detect the operation of a release switch 28 of the TV adapter 13.

The output terminals of the sequence circuit 26 are connected to a lighting circuit 29 of the light supply unit 18 and to the input terminal of a mirror driving and lamp lighting circuit 30, respectively. The lighting circuit 29 is connected to an electronic flash tube (strobe tube) 31 so as to control flashing of the flash tube 31. The mirror driving and lamp lighting circuit 30 is connected to a mirror driving solenoid 32 and an observation lamp (halogen lamp) 33.

Figure 3:
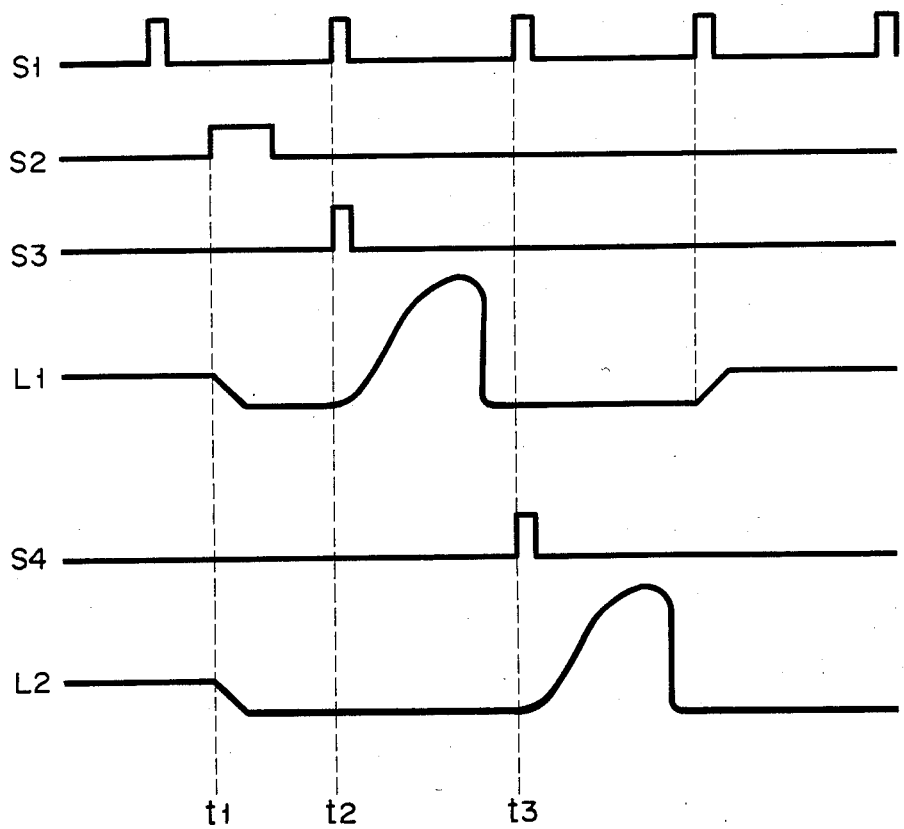
FIG. 3 is a timing chart for explaining the operation of the circuit shown in FIG. 2.

The operation of the endoscopic photographing apparatus described above will be described with reference to the timing chart in FIG. 3.

The power switch of the light supply unit 18 is turned on, and the observation lamp 33 is turned on, so that light is incident on a light guide 11a of the endoscope 11 via a mirror 34. The observation light through the light guide 11a illuminates an object 35 to be examined. Light reflected by the object 35 is transmitted through an image guide 11b and is focused as an object image on an image pickup surface of the CCD 22 of the TV camera 14. The CCD 22 converts the object image to a video signal in synchronism with a timing signal from the timing circuit 24. In this case, the CCD 22 is scanned in accordance with interlaced scanning. The video signal is supplied to the video signal processor 23 of the CCU 20 and is processed in a known manner. The video signal from the video signal processor 23 is supplied to the CRT display 21 and is displayed as the object image, i.e., a body cavity image. When the video signal is supplied to the transfer gate signal detector 25, only a transfer gate signal S1 is detected from the video signal. The transfer gate signal S1 has a signal component which is generated during the interlaced scanning period (1/60 sec). In this state, when the doctor or operator turns on the release switch 28 at time $t_1$ in order to photograph a still image, the release detector 27 detects the operation state of the release switch 28 and generates a release signal S2. When the release signal S2 is supplied to the sequence circuit 26, the sequence circuit 26 supplies a drive signal to the mirror driving and lamp lighting circuit 30 in response to the leading edge of the release signal S2. The mirror driving and lamp lighting circuit 30 energizes the mirror driving solenoid 32 to perform the mirror-up operation. At the same time, the mirror driving and lamp lighting circuit 30 turns off the halogen lamp 33. The sequence circuit 26 supplies a trigger signal S3 to the lighting circuit 29 in response to a pulse component of the transfer signal S1 appearing at time $t_2$ after the release signal S2 is generated. The lighting circuit 29 energizes the flash tube 31 in response to the trigger signal S3. When the flash tube 31 flashes for a given period, it turns off. The given period falls within the one-field scanning period, i.e., the pulse interval (1/60 sec) of the transfer gate signal S1. All light rays from the flash tube 31 are used for photographing light rays for still image photographing. In this case, when the operation of the lighting circuit 29 is delayed with respect to the trigger signal S3, the delay time must fall within a difference (i.e., 6.7 msec) between the one-field scanning period (16.7 msec) and the flashing period (10.0 msec).

When the flash tube 31 flashes and is turned off, the sequence circuit 26 supplies a restore signal to the mirror driving and lamp lighting circuit 30 in response to a transfer gate pulse. Therefore, the lamp 33 is turned on, and the mirror 34 returns to the original position, so that the observation light is guided in the light guide 11a. The endoscopic photographing apparatus is then set in the observation state.

The flash tube 31 is triggered in response to the transfer gate pulse appearing immediately after the releasing action is performed. In this case, when the OFF operation of the observation lamp 33 is delayed or the mirror-up operation is delayed, the observation light may be mixed-in the flash light, thereby resulting in a foggy image. In order to prevent this drawback, the flash tube 31 flashes after at least one-field scanning period from the time at which the transfer gate pulse appears upon the releasing action. More particularly, as shown in FIG. 3, the sequence circuit 26 generates a trigger signal S4 at time $t_3$ in response to a gate pulse which is generated next to the transfer gate pulse appearing immediately after the release signal S2 is generated. The lighting circuit 29 causes the flash tube 31 to flash in response to the trigger signal S4. Therefore, the observation light will not be mixed in the flash light, thereby preventing a foggy image. It should be noted that the light distribution is indicated by reference symbol L2.

In the above description, the start time of the flash tube is delayed by a one-field scanning period. However, it can be delayed by a two-field scanning time (i.e., one-frame) or longer.

Figure 4:
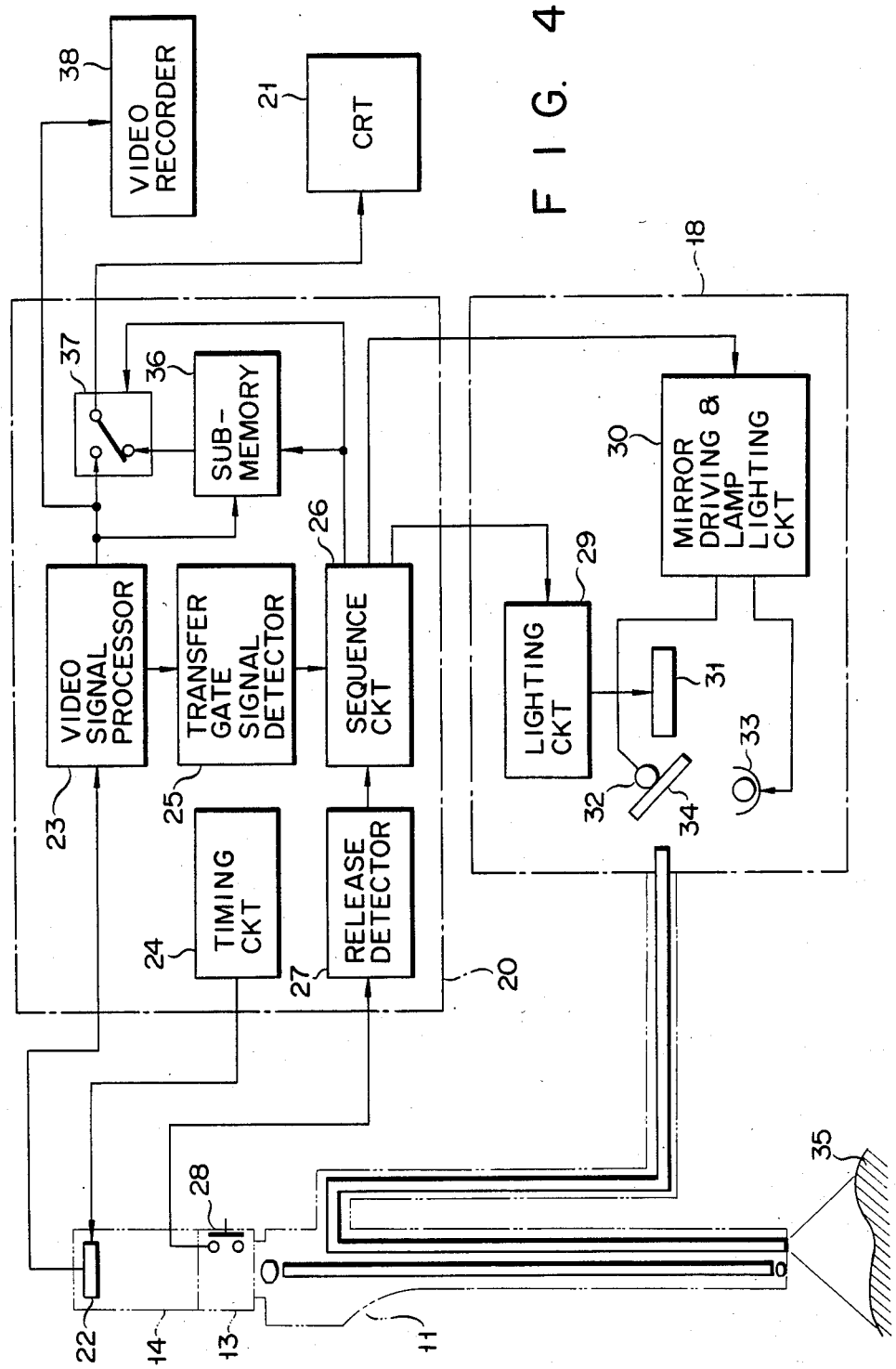
FIG. 4 is a block diagram of an endoscopic photographing apparatus according to another embodiment of the present invention.

As described above, when the dark state is provided before a still image is photographed, no image is displayed on the CRT display 21, so the observer is often anxious about this display state. In order to ease the observer, a sub-memory 36 having a CCD or CTD memory or a conventional digital memory is arranged in the CCU 20, as shown in FIG. 4. The write-in terminal of the sub-memory 36 is connected to the output terminal of the video signal processor 23, and the read-out terminal thereof is connected to one input terminal of a switch circuit 37. The other input terminal of the switch circuit 37 is connected to the output terminal of the video signal processor 23. The common terminal of the switch circuit 37 is connected to the CRT display 21. A video recorder 38 is directly connected to the output terminal of the video signal processor 23.

Figure 5:
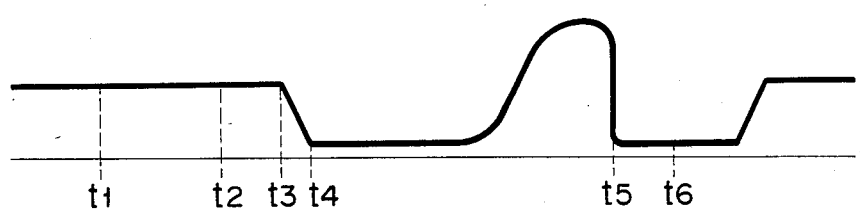
FIG. 5 is a timing chart for explaining the operation of the apparatus shown in FIG. 4.

The operation of the circuit shown in FIG. 4 will be described with reference to the timing chart in FIG. 5. In the observation mode, when the release switch 28 is operated, the release signal is supplied to the sequence circuit 26. The sequence circuit 26 causes the observation lamp 33 to turn off in response to the release signal and the mirror 34 to rise up. The halogen lamp 33 and the mirror 34 cannot be immediately operated in response to the release signal due to an operation delay. Therefore, the CCD 22 is illuminated by reflected light of the observation light from the object during a time period from $t_1$ to $t_4$. In this case, the sequence circuit 26 supplies the write-in signal to the sub-memory 36 so as to store the field video signal corresponding to the time $t_1$ in the sub-memory 36. At the same time, the sequence circuit 26 causes the switch circuit 37 to switch to the terminal connected to the sub-memory 36. Therefore, the read-out video signal from the sub-memory 36 is supplied to the CRT display 21. The video signal is then displayed as an image on the CRT display 21. The image charge obtained by the observation light during the time period from $t_1$ to $t_2$ is transferred during a time period from $t_2$ to $t_3$. The corresponding video signal is stored in the sub-memory 36. The stored video signal is supplied to the CRT display 21 at time $t_4$ through the switch circuit 37. This video signal is displayed on the CRT display 21. The observation light is completely extinguished at time $t_4$, and the body cavity will not be illuminated by light at least for the one-field scanning period so as to prevent a foggy image. In this manner, the body cavity is kept in the dark state. Only a video signal corresponding to the dark state is generated from the CCD 22 during this time period, so that the output from the CCD 22 is a signal indicating no image. When this signal is supplied to the CRT display 21, no image is displayed on the CRT display 21. However, as described before, the field video signal corresponding to the field at the time of release action is read out from the sub-memory 36 and is supplied to the CRT display 21. As a result, an image is displayed on the CRT display 21.

When a predetermined time interval, i.e., one-field scanning period, has elapsed, the sequence circuit 26 supplies a trigger signal to the lighting circuit 29, thereby flashing the flash tube 31. The CCD 22 stores image charge corresponding to the amount of the flash light. The stored charge is transferred during a time period from $t_5$ to $t_6$ and is processed. In this case, the video signal is stored in the sub-memory 36 and is displayed on the CRT display 21 through the switch circuit 37. After the flash tube 31 completes its flash, the halogen lamp 33 is turned on again and the mirror 34 returns to the original position.

In the dark state for preventing a foggy image, the image is displayed on the CRT display to ease the observer, thereby smoothly performing an endoscopic diagnosis.

In the above embodiment, the flash tube flashes for the maximum period (10.0 msec). However, the flash tube can flash for a shorter period when closeup photographing is performed.

As described in the "Background of the Invention", the flash tube flashes within a range between 1/60 sec and 1/1000 sec in the automatic flash mode. In particular, when the shutter speed is increased, the charge distribution of the CCD varies due to the influence of the dark current. The dark current of the CCD is increased when the ambient temperature is increased. When the CCD is disposed at the distal portion of the endoscope which is subject to high temperatures, the dark current cannot be neglected.

Figure 7:
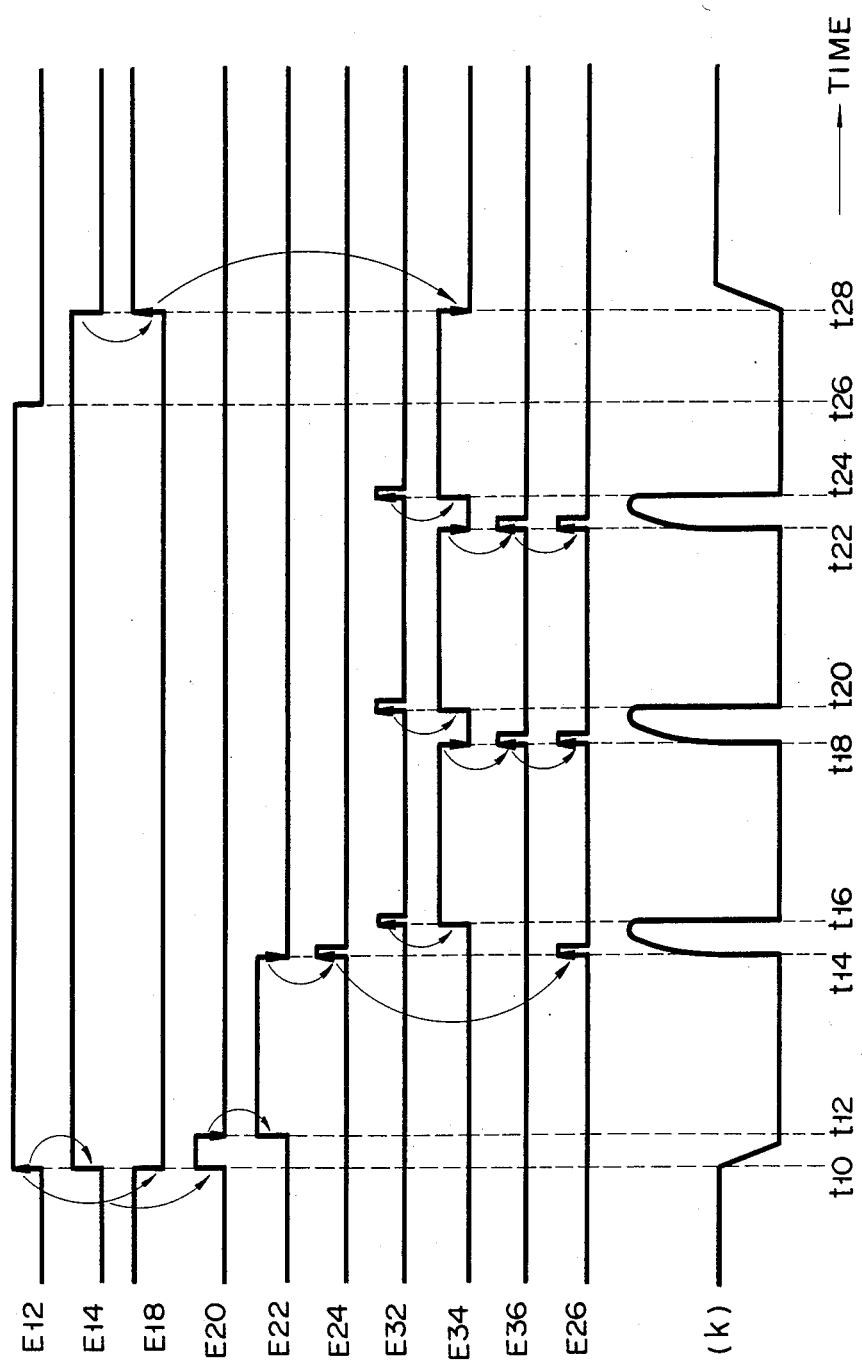
FIG. 7 is a timing chart for explaining the operation of the circuit shown in FIG. 6.

According to the embodiment of FIG. 6, when the operator depresses a release switch 28, a release signal E12 is generated from a release detector 112 at time $t_{10}$ as shown in FIG. 7. If the operator wishes to perform the motor-drive photographing, he continuously depresses the release switch 28. While the switch 28 is held in the ON state, the signal E12 is set at logic "1".

The leading edge of the release signal E12 sets an R-S flip-flop (FF) 114. A Q output E14 from the FF 114 goes to logic "1". A mirror driver 116 drives a mirror 34 to rise it up in response to E14="1". The light from the observation lamp 33 will not be guided to the light guide 11a, so that the CRT screen becomes temporarily dark (time $t_{10}$ to $t_{14}$). The signal E12 is supplied to a NOR gate 118. Since E12="1" is established, a reset output E18 from the NOR gate 118 is set at logic "0". Once the FF 114 is set in response to E12="1", it cannot be reset as long as E18="0".

The leading edge of the release signal E12 triggers a delay circuit 120 such as a one-shot multivibrator. The delay circuit 120 then generates a delay pulse E20 of logic "1". When a predetermined time interval given by a time constant of the one-shot multivibrator has elapsed, the pulse E20 goes to logic "0" (time $t_{12}$).

The trailing edge of the delay pulse E20 triggers a one-frame counter 122 (time $t_{12}$). The counter 122 starts counting pulses which correspond to one frame (one screen) of the CCD image sensor 22 and generates a transfer gate signal E22 of logic "1" during the one-frame period (time $t_{12}$ to $t_{14}$).

The gate signal E22 is supplied to a CCD controller 138. The CCD controller 138 scans the CCD 22 for the one-frame period in response to the signal E22 and performs charge transfer from the cells of the CCD 22 so as to completely discharge the CCD 22. During this period (time $t_{12}$ to $t_{14}$), no optical image is formed by the CCD 22. An image signal E40 from the CCD 22 indicates darkness. When charge transfer is completed, the gate signal E22 goes to logic "0".

The trailing edge of the gate signal E22 triggers a pulser 124 such as a one-shot multivibrator having a very small time constant. The pulser 124 then generates an impulse E24 of logic "1" (time $t_{14}$). The impulse E24 serves as a strobe trigger pulse E26 (time $t_{14}$) through an OR gate 126. The pulse E26 triggers a strobe lighting circuit 128. The lighting circuit 128 is triggered in response to the leading edge of the pulse E26 and energizes a strobe tube 130 (after time $t_{14}$).

When the exposure level of the CCD 22 which is calculated in accordance with luminance data of the CCD 22 has reached a predetermined value upon flashing of the strobe tube 130, an auto-exposure circuit 132 generates a strobe off pulse E32 of logic "1" (time $t_{16}$). When the lighting circuit 128 receives the pulse E32, it deenergizes the strobe tube 130 (time $t_{16}$). By this moment, recording of a charge distribution corresponding to the optical image of the object is completed.

The strobe off pulse E32 triggers a one-frame counter 134 (time $t_{16}$). The counter 134 generates a transfer gate signal E34 of logic "1" for a period corresponding to one frame of the CCD 22 (time $t_{16}$ to $t_{18}$).

The gate signal E34 is supplied to the CCD controller 138. When E34="1" is established, the controller 138 scans cells of one frame of the CCD 22 so as to transfer the image charge for one frame stored in the CCD 22. A video signal E38 corresponding to the image signal E40 is supplied from the CCD 22 to a video signal processor 142 through the controller 138. In this state, the cells of the CCD 22 are not charged.

The processor 142 processes the signal E38 which is then converted to an NTSC color video signal E42. This video signal E42 is supplied to a magnetic disc video recorder 144. The recorder 144 records the video signal E42 in accordance with the gate signal E34. Thus, one-frame recording is completed.

When the switch 28 is kept ON at time $t_{18}$, the release signal E12 is kept at logic "1". In this case, E18="0" is held, the FF 114 is not set, and the observation light is not incident on the light guide 11a.

The trailing end of the gate signal E34 at time t18 triggers a one-shot pulser 136 through an AND gate 135 which is open-gated in response to E12="1". An impulse E36 of logic "1" is generated from the pulser 136 (time $t_{18}$). The impulse E36 becomes the trigger pulse E26 through the OR gate 126. The lighting circuit 128 is triggered in response to the trigger pulse E26. The second strobe light is emitted after time $t_{18}$.

When the predetermined exposure operation is completed, a strobe off pulse E32 is generated from the auto-exposure circuit 132 (time $t_{20}$). The strobe flashing is stopped in response to the pulse E32 (time $t_{20}$). At this moment, the CCD 22 completes recording of the charge distribution of the second object image.

The counter 134 is triggered again in response to the pulse E32 and generates the gate signal E34 (time $t_{20}$ to $t_{22}$) during a one-frame period. The charge representing the second object image is recorded in the recorder 144 in response to the gate signal E34.

When E12="1" at time $t_{22}$, the same operation as in the time period from $t_{18}$ to $t_{22}$ is performed, and the third object image is recorded.

When the switch 28 is turned off immediately after the third flashing operation is completed, the release signal E12 goes to logic "0" (time $t_{26}$). One input terminal of the NOR gate 118 is set at level "0" (E12="0"). When the counter 134 completes the third counting operation and the recorder 144 finishes recording the third object image, the gate signal E34 goes to logic "0" (time $t_{28}$). The two input terminals of the NOR gate 118 are set at logic "0", and the reset output E18 is set at logic "1" (time $t_{28}$). The FF 114 is reset in response to the signal E18="1", and the Q output E14 goes to logic "0" (time $t_{28}$). As a result, the object is illuminated again by the observation light (after time $t_{28}$).

Since E12="0" at time $t_{28}$, the AND gate 135 is closed. The pulser 136 will not be thus triggered by the gate signal E34, and the pulses E36 and E26 will not be generated (time $t_{28}$). For this reason, strobe flashing will not occur after the switch 28 is turned off (after time $t_{26}$) unless the switch 28 is depressed again.

The above description is concerned with a motor-drive operation. However, a single picture can be taken in the following manner. The release detector 112 comprises a one-shot multivibrator which is triggered when the release switch 28 is turned on. The one-shot multivibrator generates a release signal E12 which goes to logic "1" immediately after the switch 28 is turned on. When a predetermined time interval has elapsed after that, the signal E12 goes to logic "0". The time constant of the multivibrator is determined such that the signal E12 goes to logic "0" during a time period from $t_{16}$ to $t_{18}$, thereby taking a single picture.

According to the embodiments of the present invention, charge can be transferred immediately after it is stored (e.g., at time $t_{16}$ in FIG. 7), irrespective of motor-drive mode or single picture mode, so that the CCD tends not to be influenced by the dark current. Therefore, the endoscopic photographing apparatus of the present invention is also suitable for high-speed photographing.

Figure 8:
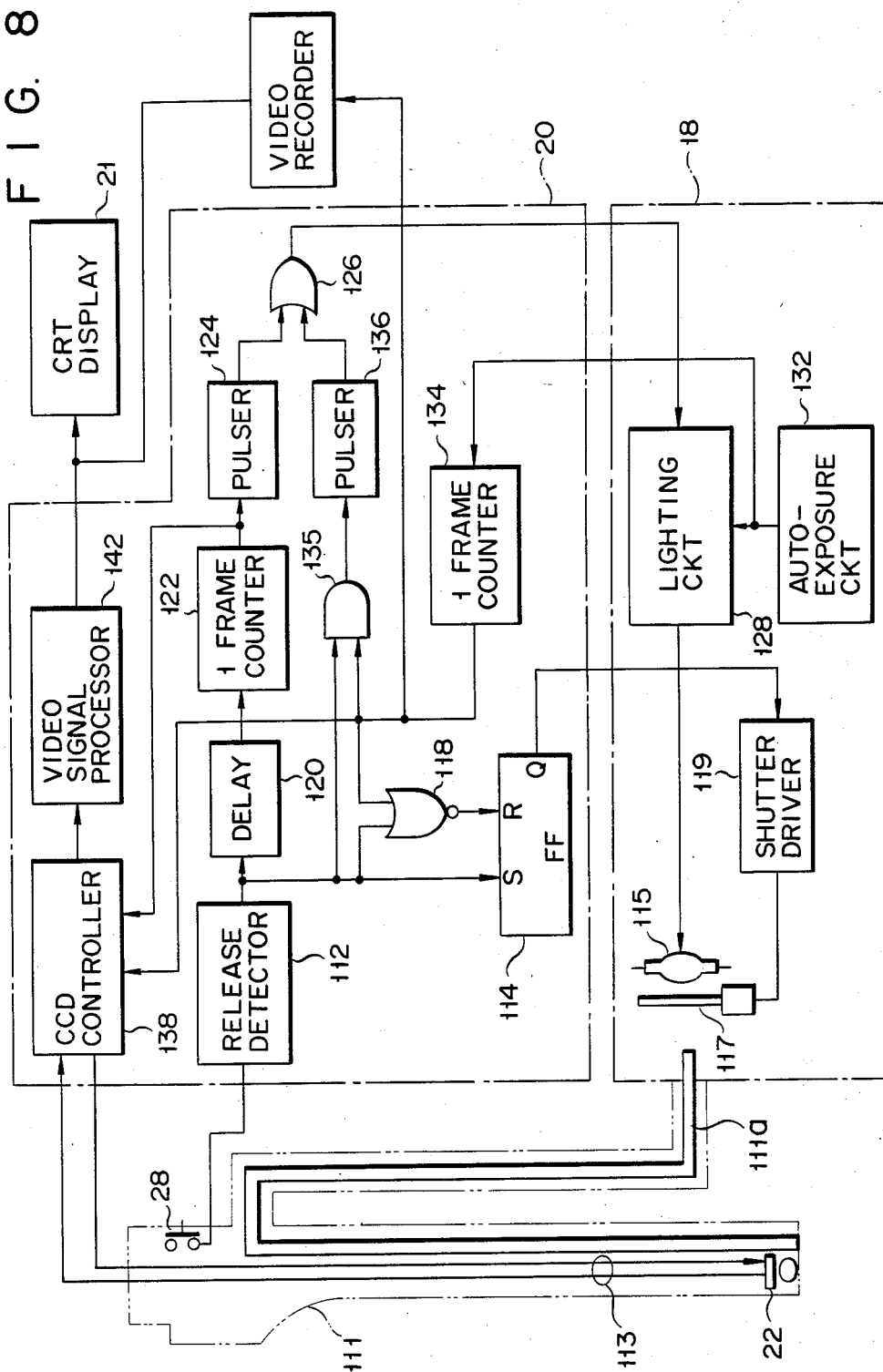
FIG. 8 is a block diagram of an endoscopic photographing apparatus according to still another embodiment.

FIG. 8 shows another embodiment of the present invention, an endoscopic photographing apparatus using an endoscope 111 with a CCD 22 built in the distal portion. In this embodiment, CCD 22 is connected to the CCD controller 138 of a CCU 20 by a line 113 which extends through endoscope 111. A short arc xenon lamp 115 (i.e., a light source), which can function as a flash tube, is provided in a light supply unit 18. A shutter 117 is disposed between the lamp 115 and the light guide 11a of endoscope 111. The shutter 117 is actuated by a shutter driver 119 which acts in response to an output from a flip-flop 114.

When the apparatus of FIG. 8 is set to the observation mode, lamp 115 is lighted by a lighting circuit 128 and emits a predetermined amount of light. When a release switch 28 is pushed in the observation mode, flip-flop 114 is set by the signal from the release detector 112. Shutter driver 119 drives shutter 117 in response to a set signal from flip-flop 114, thereby preventing the light from reaching light guide 111a. At this time the view field of the endoscope becomes dark, and the residual charge is removed from CCD 22 as in the embodiment of FIG. 6. The moment the shutter 117 is opened, lighting circuit 128 causes lamp 115 to flash. The light from the lamp 115 is guided by light guide 111a into the body cavity of the patient. The image of the object within the body cavity is thus formed on CCD 22. When the exposure of the object reaches a predetermined value, an autoexposure circuit 132 produces an output. In response to this output, the flashing of lamp 115 is interrupted and the shutter 117 is closed. The charge accumulated in CCD 22 is then immediately transferred as an image signal to the CCD controller 138. This image signal is processed in the same way as in the embodiment of FIG. 6, thus forming a video signal. The video signal is input to the video recorder 144 and thus recorded.

As mentioned above, in the embodiment of FIG. 8, the charge accumulated in CCD 22 is transferred to the CCD controller 138 right after the photographing. Accordingly, the photographing is not adversely influenced by dark current at all.

What is claimed is:

1. An endoscopic photographing apparatus including an endoscope having a distal portion adaptable for placement adjacent to a given object, said apparatus comprising:

light source means coupled to said endoscope having a distal portion, for selectively providing observation light and photographing light to the endoscope, said light source means comprising an observation light source for normally continuously emitting an observation light through said endoscope and out of said distal end toward said given object and a photographing light source for selectively generating the photographing light through said endoscope and out said distal end toward said object;

photographing means coupled to the endoscope and comprising a solid state image sensor for converting an optical image obtained from the distal portion of the endoscope to a video signal, and means coupled to said image sensor for generating a synchronous signal component to be associated with said video signal;

releasing means, operable in a still photographing mode, for generating a release signal; and light source energizing means coupled to said releasing means for preventing the observation light source from emitting light toward said given object in response to said release signal and for energizing said light source means in timed response to the release signal and the synchronous signal component of the video signal to generate the photographing light, including means for causing the light source means to provide said photographing light, after the observation light has been prevented from emitting light toward said given object, in response to a synchronous signal component generated only after lapse of at least one field scan period following generation of the next previous synchronous signal component which is generated immediately after generation of said release signal.

2. An apparatus according to claim 1, wherein said observation light source comprises a halogen lamp.

3. An apparatus according to claim 1, wherein said photographing light source comprises an electronic flash tube.

4. An apparatus according to claim 1, further comprising: storage means for storing the video signal obtained on the basis of the observation light at the time of generation of the release signal in response to the release signal from said releasing means; and displaying means for displaying the video signal stored in said storage means until at least the still image is photographed.

5. An apparatus according to claim 1, further comprising a video recorder for recording the video signal of said photographing means.

6. An apparatus according to claim 1, further said solid state image sensor comprises a CCD image sensor.

7. An apparatus according to claim 1, wherein said photographing means comprises a television camera mounted on an eyepiece section of the endoscope.

8. An apparatus according to claim 1, wherein said solid state image sensor is provided in the distal portion of said endoscope.

9. An apparatus according to claim 1, wherein said light source means comprises a short arc xenon lamp for selectively generating the observation light and photographing light.

10. An endoscopic photographing apparatus including an endoscope having a distal portion adaptable for placement adjacent to a given object, said apparatus comprising:
light source means adapted to be coupled to said endoscope having a distal portion, for selectively providing observation light and photographing light to the endoscope;
photographing means adapted to be connected to the endoscope and comprising a solid state image sensor for converting an optical image obtained from the distal portion of the endoscope to a video signal having image information components, and means coupled to said image sensor for generating a synchronous signal component to be associated with said video signal;
releasing means operable in a still photographing mode for generating a release signal;
light source energizing means coupled to said releasing means for energizing said light source means in timed response to the synchronous signal component and the release signal to cause said light source means to generate the photographing light;
detecting means for detecting an end of emission of the photographing light; and
reading means for reading out the image information components of the video signal from said solid state image sensor immediately after said detecting means completes the detecting operation.

11. An apparatus according to claim 10, wherein said light source means comprises an observation light source for continuously emitting the observation light and a photographing light source for generating the photographing light.

12. An apparatus according to claim 11, wherein said observation light source comprises a halogne lamp.

13. An apparatus according to claim 11, wherein said photographing light source comprises an electronic flash tube.

14. An apparatus according to claim 10, further comprising: storage means for storing the video signal obtained on the bassis of the observation light at the time of generation of the release signal in response to the release signal from said releasing means; and displaying means for displaying the video signal stored in said storage means until at least the still image is photographed.

15. An apparatus according to claim 10, further comprising a video recorder for recording the video signal of said photographing means.

16. An apparatus according to claim 10, wherein said solid state image sensor comprises a CCD image sensor.

17. An apparatus according to claim 10, wherein said photographing means comprises a television camera mounted on an eyepiece section of the endoscope.

18. An apparatus according to claim 10, wherein said solid stage image sensor is provided in the distal portion of said endoscope.

19. An apparatus according to claim 10, wherein said light source means comprises a short arc xenon lamp for selectively generating the observation light and photographing light.

* * * * *